US008586946B2

(12) United States Patent
Beck et al.

(10) Patent No.: US 8,586,946 B2
(45) Date of Patent: Nov. 19, 2013

(54) TEST APPARATUS FOR AN OPTICAL INVESTIGATION SYSTEM

(75) Inventors: Gerd Beck, Wurmlingen (DE); Bernhard Gloeggler, Tuttlingen (DE); Andre Ehrhardt, Wurmlingen (DE)

(73) Assignee: Karl Storz GmbH & Co. KG (DE)

( * ) Notice: Subject to any disclaimer, the term of this patent is extended or adjusted under 35 U.S.C. 154(b) by 95 days.

(21) Appl. No.: 12/969,891

(22) Filed: Dec. 16, 2010

(65) Prior Publication Data
US 2011/0140003 A1    Jun. 16, 2011

(30) Foreign Application Priority Data
Dec. 16, 2009    (DE) .......................... 10 2009 058 660

(51) Int. Cl.
*G01J 1/58*    (2006.01)
(52) U.S. Cl.
USPC ....................................... 250/459.1
(58) Field of Classification Search
USPC ....................................... 250/459.1
See application file for complete search history.

(56) References Cited

U.S. PATENT DOCUMENTS

| | | | | |
|---|---|---|---|---|
| 5,820,547 | A * | 10/1998 | Strobl et al. | 600/127 |
| 6,361,490 | B1 * | 3/2002 | Irion et al. | 600/175 |
| 6,511,418 | B2 * | 1/2003 | Shahidi et al. | 600/117 |
| 6,807,876 | B2 * | 10/2004 | Beck et al. | 73/865.9 |
| 2003/0078477 | A1 | 4/2003 | Kang et al. | |
| 2003/0105195 | A1 | 6/2003 | Holcomb et al. | |

FOREIGN PATENT DOCUMENTS

| | | |
|---|---|---|
| DE | 9320491 U1 | 8/1994 |
| DE | 19638809 A1 | 4/1998 |
| DE | 19855853 A1 | 6/2000 |
| DE | 102008018637 A1 | 10/2009 |
| DE | 102008049922 A1 | 4/2010 |
| EP | 1728464 A1 | 12/2006 |
| WO | 9711636 A2 | 4/1997 |

OTHER PUBLICATIONS

European Search Report; Application No. EP 10 19 4669; Mar. 22, 2011; 7 pages.

* cited by examiner

*Primary Examiner* — Marcus Taningco
(74) *Attorney, Agent, or Firm* — St. Onge Steward Johnston & Reens LLC (57) ABSTRACT

A test apparatus for an optical investigation system, with an imaging device and a light source for optical investigation of an object in remitted light and/or fluorescent light includes a housing with a hollow space and an aperture for inserting a distal end of the imaging device into the hollow space, a reference surface with predetermined optical properties in the hollow space, at least either for remission of illuminating light directed onto the reference surface or for emission of fluorescent light, and a positioning device to hold the imaging device of the distal end of the imaging device at a predetermined position in relation to the reference surface.

19 Claims, 6 Drawing Sheets

TEST APPARATUS FOR AN OPTICAL INVESTIGATION SYSTEM

CROSS-REFERENCE TO RELATED APPLICATIONS

The present application claims priority of German patent application No. 10 2009 058 660.1 filed on Dec. 16, 2009.

FIELD OF THE INVENTION

The present invention relates to a test apparatus for an optical investigation system, with a light source and an imaging device for optical investigation of an object inside and outside the field of medicine. The present invention relates in particular to a test apparatus for an endoscopy system with a light source and an endoscope.

BACKGROUND OF THE INVENTION

Endoscopy systems, consisting of an endoscope and a light source, are used for endoscopy in medical or non-medical applications—in the latter case also known as boroscopy. The light source can be integrated in the endoscope, in particular in its distal end, or can be present as a separate unit, which is optically coupled with an endoscope by a light conductor cable. Light from the light source emerges at the distal end of the endoscope and there illuminates an object to be investigated. Light remitted by the object is captured by a lens on the distal end of the endoscope and conducted onto a light-sensitive image sensor or conveyed, for example by means of an oriented bundle of lightwave conductors or a rod lens system, to the proximal end of the endoscope. In the latter case the light remitted by the object can be observed on the proximal end of the endoscope by an eyepiece or is recorded by means of a video camera. As an alternative or in addition to remitted light, light emitted by the object can also be observed, in particular fluorescent light.

The quality of an image recorded by an endoscopy system, in particular brightness, brightness-color contrast, signal-noise ratio, color fidelity and resolution or sharpness, depend on the observed object, in particular its optical properties, and above all on the endoscopy system. Relevant factors are, for example, the functionality of the light source, its radiant capacity or the light beam generated by it, the spectrum of generated light, in some cases the transmission properties of an employed light conductor cable and the coupling of the light conductor cable with the light source and with the endoscope, the functionality of the light transmission within the endoscope, the degree of effectiveness of the uncoupling of light from the light source out of the endoscope, the functionality or optical properties of the observation beam path in the endoscope, possibly including an oriented bundle of lightwave conductors or a rod lens system, the functionality of the eyepiece or video camera. Frequent sources of failure are, among others, the light source subjected to an alteration process, possibly the light conductor cable and its coupling to the light source and the endoscope, and the coupling of a video camera to the endoscope.

Fluorescent light is observed for medical-diagnostic purposes in particular. In photodynamic diagnostics (PDD), for example, a fluorescence of protoporphyrin IX induced by administered 5-aminolevulinic acid (ALA) is observed. Enrichment of ALA and thus also the intensity of the fluorescence depend on the condition of the tissue. In autofluorescence diagnostics (AF diagnostics) the fluorescence of bodily-produced fluorophores is observed, whose concentration is likewise dependent on the condition of the tissue. Fluorescent diagnostic methods are used in fields other than medicine as well.

To prevent remitted excitation light or illuminating light from outshining the fluorescence, an illumination filter is used in the illumination or excitation beam path between light source and object and in the observation beam path between object and video camera or eyepiece. The illumination filter is a short pass filter, which essentially transmits only the short wavelengths required to excite the fluorescence, but on the other hand primarily or almost exclusively reflects or absorbs longer wavelengths. A very reduced, but not disappearing, transmission in the blocking range is desired with many applications in order to receive, even without fluorescence, an image that has a low brightness but is visible. The observation filter is a long pass filter that transmits only wavelengths of fluorescence and reflects or absorbs short-wave excitation light remitted by the object. Illumination or excitation filters can as a rule be manually or mechanically exchanged or changed. Observation filters can be replaceable or changeable, but in many case are firmly built into the endoscope. In urology, for example, for observation in white light, ALA or AF fluorescence, various endoscopes are used that, at least in the observation beam path, are optimized for their respective use or have a corresponding filter characteristic. The aforementioned sources of failure or influences on functionality of the endoscopy system include, in the case of observation of fluorescence, the combination of the illumination filter or spectrum of the light source on the one hand and of the observation filter on the other hand.

A corresponding problem exists with other optical investigation systems, which include an imaging device and a light source for optical investigation of medical and non-medical objects in remitted light and/or in fluorescent light. These include exoscopes, which for instance are used for diagnostics and for microsurgical procedures on or close to bodily surfaces.

DE 196 38 809 A1 describes a device for testing and/or adjusting a PDD or PDT (photodynamic therapy) system and/or for training on a system of this type. Positioned in a housing is a target, opposite to which a distal end of an endoscope can be mounted. The curvature of the target can correspond to the variable field curvature of an imaging unit of the endoscope. A photo element and light sources are provided in the target. The photo element records the illuminating strength of an illuminating light emitted from the endoscope. A control guides the light sources as a function of the illuminating strength recorded by the photo element.

DE 198 55 853 A1 describes an apparatus for testing and/or adjusting a PDD or PDT system and/or for training on a system of this type. The apparatus includes a luminescent phantom with a fluorescent dye. One end of an endoscope can be positioned opposite the luminescent phantom.

In the post-published DE 10 2009 043 696, an apparatus and a method for testing endoscopes are described. The apparatus includes a filter module with several perforations in which optical filters are positioned. The filter module is illuminated from one direction by the light source via a light conductor cable. From an opposite direction the light transmitted by the filter module is observed by means of an endoscope.

Depending on concrete challenges arising in practice, each of the apparatuses and methods known to date can include advantages and disadvantages. For example, under certain circumstances and for some applications, none of the apparatuses and methods here described makes possible a reliable and possibly even quantitative test of a complete endoscopy system or of another complete optical investigation system in precisely the condition in which it has been or is used medically or non-medically before or since.

SUMMARY OF THE INVENTION

An objective of the present invention consists in providing an improved test apparatus and an improved method for testing an optical investigation system that in particular simplify an absolute and precise test of the functionality or of another property of the optical investigation system.

This object is achieved through the contents of the independent claims.

Elaborations are indicated in the dependent claims.

Embodiments of the present invention are based on the idea, in a test apparatus for an optical investigation system with an imaging device and a light source, of providing a positioning device to hold the imaging device in a predetermined position and in particular in a predetermined direction of the distal end of the imaging device to a reference surface of the test apparatus. For this purpose the positioning apparatus in particular comprises a mechanical stop that is configured in such a way that the distal end of an imaging device inserted into the test apparatus stands at a predetermined position, in particular also at a predetermined distance to the reference surface, when the imaging device comes into contact with the stop.

The positioning device makes possible, in a simple manner, a reproducible and precise positioning of the distal end of the imaging device in relation to the reference surface of the test apparatus. The test apparatus can thus be used not only for training purposes or for a qualitative measurement or testing of the functionality of an optical investigation system, but also for a quantitative test. Because of the precise and reproducible positioning of the distal end of the imaging device in relation to the reference surface of the test apparatus, it becomes possible to draw quantitative conclusions concerning the functionality and other properties of the optical investigation system, for example from the brightness of the image of the reference surface generated by the imaging device. If the image of the reference surface generated by the imaging device is too dark, it can no longer stand at a false positioning of the distal end of the imaging device in relation to the reference surface. Instead, there must be a defect in the optical investigation system, for example a light source that is no longer functional or not completely functional, a defective light conductor cable, or a faulty coupling between a light conductor cable and the light source or imaging device.

A test apparatus for an optical investigation system with an imaging device and a light source for optical investigation of an object in remitted light and/or in fluorescent light includes a housing with a hollow space and an aperture for inserting a distal end of the imaging device into the hollow space, a reference surface with predetermined optical properties in the hollow space at least either for remission of illuminating light falling on the reference surface or for emission of fluorescent light, and a positioning device to hold the imaging device at a predetermined position of the distal end of the imaging device in relation to the reference surface.

The test apparatus is in particular a test apparatus for an endoscopy system with an endoscope and a light source. The light source can be integrated into the endoscope or be present as a separate unit. In the latter case the light source, for example by means of a light conductor cable, can be coupled with the imaging device, so that the imaging device is configured to transmit illuminating light from the light source to the distal end of the imaging device. Alternatively the optical investigation system can be configured in order to conduct illuminating light from the light source via an illumination beam path outside the imaging device to an object that is to be investigated or observed.

The reference surface can be flat or curved, in particular concave. The predetermined optical properties of the reference surface are in particular unchanging or stable over time. The optical properties of the reference surface include in particular the remission factor as a function of the wavelength of illuminating light and in some cases a fluorescence quantity yield as a function of the excitation wavelength and of the wavelength of the emitted fluorescent light. Concerning its remission properties, the reference surface is, for example, approximately a Lambertian radiator with an approximately ideally diffuse remission.

The positioning device can be replaceable to permit operation of the test apparatuses with different imaging devices. In addition, the positioning device can be configured to shield the hollow space of the housing of the test apparatus from the incidence of ambient light, at least when an imaging device is inserted into the test apparatus. The position of the distal end of the imaging device in relation to the reference surface of the test apparatus, as predetermined by the positioning device, in particular the distance between the two, can be selected so that the relative position corresponds to a typical position of the distal end of the imaging device during an optical investigation of an object. The test apparatus thus makes possible a testing of an optical investigation system under realistic conditions.

To allow testing of an optical investigation system under the most realistic conditions possible, the test apparatus can in addition be configured to contain water or another fluid whose refractive index is greater than 1. For this purpose the test apparatus and in particular the housing and positioning device are configured in such a way that the fluid does not escape, or at least does so only slowly, when an imaging device is inserted into the test apparatus. The housing and positioning device include for this purpose, for example, O-rings or other insulations. If the test apparatus is configured to contain a liquid, the aperture to the hollow space in the housing can be positioned in an upper area, in particular at the highest point of the hollow space. This makes possible, for example, a simulation of the conditions that prevail in urology during an endoscopic investigation of a bladder filled with urine.

The positioning device, in addition, can be configured so as to prevent an imaging device that is inserted into the test apparatus from rotating around its longitudinal axis. For this purpose the positioning device includes in particular a device for force-locked or form-locked blocking of a rotation of an imaging device, for example a ball catch-locking apparatus. This device can simultaneously be configured to hold an imaging device inserted into the test apparatus, in particular its distal end, in a predetermined position. Preventing rotation of an imaging device in the test apparatus around its longitudinal axis can be advantageous, especially with the imaging device at a non-axial viewing direction, to ensure that the imaging device is aimed at the reference surface or in some cases at a determined reference point such as a mark on the reference surface.

A test apparatus as described here can be configured in such a way that the positioning device, without use of a tool, can be separated from the housing of the test apparatus and reattached with it again. For this purpose, in particular on the housing of the test apparatus, a ball catch-lock device is provided that can engage in a recess or indentation on the positioning device in order to hold the positioning device on the housing of the test apparatus. This allows not only a simple, rapid dismantling of the test apparatus for cleaning and sterilization, but also a rapid exchange of the positioning device to adapt the test apparatus to different imaging devices.

A test apparatus as described here, in particular a test apparatus in which the positioning device can be separated from the housing without the use of a tool, can include devices on the housing and on the positioning device for form-locked prevention of a rotation of the positioning device around its longitudinal axis in relation to the housing. Such devices include, for example, a pin or other convex device on the housing, which engages in a longitudinal groove or other concave device on the positioning device. This supports a defined alignment of the distal end of the imaging device in relation to the reference surface. The defined alignment of the distal end of the imaging device in relation to the reference surface can be advantageous, among other ways, in case of a non-spherical reference surface and in case of marks or other features on the reference surface on which the imaging device is to be aligned.

A test apparatus as described here, in particular a test apparatus in which the positioning device can be separated without the use of a tool from the housing and reattached with it again, can include a catch-lock device, in particular a ball catch-lock device that is configured to detachably secure the positioning device on the aperture or housing of the test apparatus.

The positioning device of a test apparatus as described here can include a holding device, in particular a spherical catch, on its end facing away from the hollow space, for catch-locked holding of the proximal end of an imaging device inserted into the test apparatus. This holding device is, for example, a ball catch-lock device that can engage in a recess or indentation on the proximal end of an imaging device. A few imaging devices, in particular endoscopes, originally comprise a recess or indentation of this type for other purposes. In particular with an endoscope with a shaft with a defined or standardized length, fixing the position of the proximal end of the imaging device can lead unavoidably to a predetermined position of the distal end of the imaging device. Here the imaging device must comprise no features on its distal end that allow a form-locked holding of the imaging device, but instead can have, for example, a simple cylindrical shape.

The reference surface is, in particular, configured in such a way that, for one or more different lines of vision of an imaging device inserted into the test apparatus, the tangential surface is situated on the reference surface in the point of intersection of the line of vision with the reference surface perpendicular to the line of vision. In addition, the reference surface can be configured in such a way that the distance between the predetermined position of the distal end of the imaging device and the particular point of intersection of the line of vision with the reference surface is equal for several different lines of vision. The line of vision is the direction facing from the distal end of the imaging device, in which an object lies that is in the center of an image generated by the imaging device.

The reference surface can constitute a portion of a spherical surface, so that the position foreseen for the distal end of the imaging device lies on the center point of the spherical surface. The distal end of the imaging device is understood in this context to mean in particular the object-side main point or point of intersection of the optical axis with the object-side principal plane of the imaging device. With a spherical-shaped configuration of the reference surface, it can be assumed that an image device inserted into the test apparatus can rotate freely around its longitudinal axis. In particular in this case, the positioning device must not be configured to prevent a rotation of the imaging device.

Alternatively the reference surface can constitute a portion of a cylindrical surface, so that the position foreseen for the distal end of the imaging device is contiguous with the axis of symmetry of the cylindrical surface. The curvature or the radius of the reference surface can be adapted to the object field curvature of the imaging device, which in turn is typically adapted to the expected use of the optical investigation system. The radius of the spherical surface or of the cylindrical surface therefore, for many uses, equals at most 100 mm and is in particular in the range between 10 mm and 50 mm or even in the range of 5 mm or less all the way to contact endoscopy. Spherical surfaces and cylindrical surfaces can be generated with comparative little difficulty and make possible a defined distance of the reference surface from the distal end of the imaging device even when the test apparatus is used for imaging devices with different lines of vision.

If the reference surface constitutes a spherical surface, the reference surface can be configured so that two opposite sites on the edge of the reference surface lie on a straight line that forms an angle between 40 and 80 degrees to the longitudinal axis of an imaging device held by the positioning device. In particular, the angle lies in the range of 50 to 70 degrees. If the reference surface constitutes a portion of a spherical surface, in particular if it is semispherical, the edge of the reference surface can lie in a plane whose normal constitutes an angle in the range of 10 to 50 degrees to the longitudinal axis of an imaging device held by the positioning device. The angle between the normals of the plane and of the longitudinal axis of the positioning device lies in particular in the range of 20 to 40 degrees, for example at 30 degrees. If the reference surface constitutes a portion of a cylindrical surface, a straight line through two opposite points on the edge of the reference surface, or a plane that contains two opposite straight portions of the edge of the reference surface, forms an angle between 40 and 80 degrees with the longitudinal axis of an imaging device held by the positioning device. The angle is in particular in the range of 50 to 70 degrees, for example at 60 degrees.

A test apparatus with a reference surface of this configuration is appropriate for testing optical investigation systems with imaging devices with different lines of vision. The test apparatus can thus be used, for example, for most endoscopes with a large number of different lines of vision without requiring the reference surface to be changed.

A test apparatus as described here can, in particular, be partly disassembled and can be completely sterilized. In particular, the reference surface and positioning device can also be sterilized without restriction. An imaging device can therefore still be tested by the test apparatus immediately before the imaging device is put to medical use and without any need to sterilize it again after the test.

The reference surface of a test apparatus as described here is white or comprises a sufficiently large white area for a white balance. This means in particular that the remission factor of the reference surface or of its white area in the wavelength range visible to the human eye—apart from at most the small wavelength ranges—is high, for example at least equal to 80%. In particular, the reference surface is a surface of a body of filled polytetrafluorethylene or silicon. The reference surface is thus also suited for performing a white balance. Polytetrafluorethylene is marketed by DuPont, among others, under the name Teflon, has optical properties that are stable or unchanging over time, and can be autoclaved without problems.

Alternatively, the reference surface is gray or colored and/ or has one or more gray or colored areas. The remission factor and/or the color and/or the fluorescent properties of the reference surface or of parts thereof can be adapted to typical or average remission factors or color shades or color values or fluorescent properties of relevant objects that are to be investigated. In particular, the optical properties of the reference surface or of one or more areas thereof can be duplicated from the median optical properties of biological tissue. In addition, the optical properties of the reference surface can be structured to duplicate, for instance, blood vessels or other structures of biological tissue.

In a method for testing an optical investigation system with an imaging device and a light source for optical investigation of an object in remitted light and/or fluorescent light, the distal end of the imaging device is inserted through an aperture into a hollow space in a housing of a test apparatus. Upon insertion or thereafter, the distal end of the imaging device is situated in the hollow space at a predetermined position relative to a reference surface with predetermined optical properties. The reference surface is illuminated by the imaging device with illuminating light with a predetermined illumination spectrum. Light remitted by the reference surface is recorded by the imaging device. The functionality or another property of the optical investigation system is determined on the basis of the recorded remitted light.

The test method is executed in particular with one of the test apparatuses described here.

BRIEF DESCRIPTION OF THE DRAWINGS

Hereinafter, embodiments are explained with reference to the appended drawings, which are as follows.

DETAILED DESCRIPTION OF THE INVENTION

Figure 1:
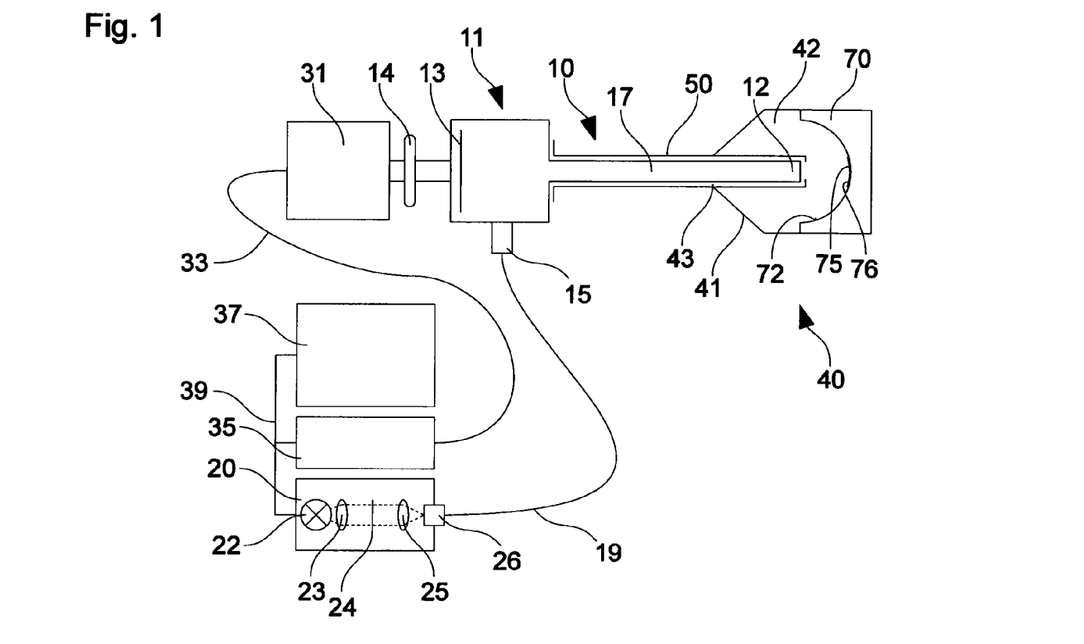
FIG. 1 is a schematic depiction of an optical investigation system.

FIG. 1 shows a schematic depiction of an optical investigation system. The optical investigation system in this example is an endoscopy system, which can be applied, for example, in medical-diagnostic methods in urology and in other specialties. The endoscopy system includes an endoscope 10 with a proximal end 11 and a distal end 12. The endoscope 10 includes an illumination or excitation beam path and an observation beam path, which are not shown in detail in FIG. 1. The illumination beam path includes in particular one or more lightwave conductors to transmit illumination or excitation light from the proximal end 11 to the distal end 12 and a light outlet on the distal end 12 through which illumination light can exit from the distal end 12 of the endoscope 10 in order to illuminate an object to be observed. The observation beam path includes a light inlet on the distal end 12 of the endoscope 10, a lens to transmit observation light emitted from an observed object, from the distal end 12 to the proximal end 11, an observation filter 13 and an eyepiece 14. To transmit the observation light from the distal end 12 to the proximal end 11 of the endoscope 10, a rod lens system, for example, or an oriented bundle of lightwave conductors is provided in a shaft 17 of the endoscope 10. The endoscope 10 in addition comprises on its proximal end 11 a coupling 15 for mechanical and optical coupling of a light conductor cable 19 with the described illumination beam path in the endoscope 10.

The endoscope 10 is coupled with a light source apparatus 20 by the light conductor cable 19. The light source apparatus 20 includes a light source 22, for example a halogen lamp, a high-pressure gas discharge lamp, a light diode or a laser. In addition the light source apparatus 20 includes a first converging lens 23, an illumination filter 24 and a second converging lens 25. The light source 22 is coupled with the light conductor cable 19 by the first converging lens 23, the illumination filter 24, the second converging lens 25 and a coupling 26.

A video camera 31 is coupled mechanically or optically by the eyepiece 14 with the endoscope 10 and its observation beam path. The video camera 31 includes a light-sensitive image sensor, for example a CCD or CMOS sensor, to convert light falling onto the image sensor into analog or digital electrical signals. By means of a signal cable 33, the video camera 31 is coupled with a camera control unit 35, designated as CCU, to transmit analog or digital electrical or optical signals.

The light source apparatus 20, camera control unit 35, and a screen 37 are coupled with one another by a communication bus 39 or several separate signal lines. By means of the communication bus 39, additional apparatuses, not shown in FIG. 1, can be coupled with the light source apparatus 20, the camera control unit 35 and the screen 37 inside or outside the treatment area in which the endoscope system is installed; examples include a database, a keyboard, a computer mouse and other user interfaces.

Also shown in FIG. 1 is a test apparatus 40 with a light-insulated housing 41, a hollow space 42 in the light-insulated housing 41 and an aperture 43 to the hollow space 42. The distal end 12 of the endoscope 10 is introduced through the aperture 43 into the hollow space 42 of the test apparatus 40. A positioning device 50 located in the aperture 43 holds the shaft 17 of the endoscope 10 by form-locking or force-fitting, in such a way that the distal end 12 of the endoscope 19 is positioned in a predetermined position and in a predetermined direction in the hollow space 42. In addition, the positioning device 50, at least when the shaft 17 of the endoscope 10 is mounted in the positioning device 50, to a great extent prevents the penetration of light from the environment through the aperture 43 into the hollow space 42 in the housing 41.

In addition, a reference body 70 with a reference surface 72 is positioned in the hollow space 42 of the test apparatus 40. The reference surface 72 has predetermined optical properties and the spatial shape of a portion of a spherical surface or of a cylindrical mantle. The position foreseen for the distal end 12 of the endoscope 10 is situated in particular at the center point of this spherical surface or on the axis of symmetry of the cylindrical mantle. In particular, the main point on the object side, or the point of intersection of the optical axis with the object-side principal plane of the imaging device 10, stands at the center point of the spherical surface or on the axis of symmetry of the cylindrical mantle.

The reference surface 72 has predetermined optical properties that are unchangeable or stable over time. The reference surface 72 can be white or can have a remission factor that is essentially wavelength independent in the spectral range visible to the human eye. The reference surface 72 can alternatively be in color or can have a wavelength dependent remission factor in the spectral range visible to the human eye. Alternatively or in addition, the reference surface 72 can be fluorescent. Here the wavelengths that are required for excitation of fluorescence, are situated for example, in the ultraviolet or, preferable for medical applications, in the blue spectral range and the emitted fluorescent light is in the green, red or infrared spectral range. The optical properties can be homogeneous or location-independent over the entire reference surface 72.

Alternatively the reference surface comprises several areas with various optical properties. In the example shown in FIG. 1, the reference surface 72 is predominantly white with an indicator area 75 and a reference area 76, which each have optical properties that differ from those of the rest of the reference surface 72. The indicator area 75 and reference area 76, with sharp edges or on the basis of their arrangement or shape, can simplify or make possible a focusing or a selection of the focal distance or size of the field of vision of the imaging device. In addition the optical properties of the indicator area 75 and of the reference area 76 can simplify a determination of the transmission spectrum of the illumination filter 24 and of the transmission spectrum of the observation filter 13.

The reference body 70, apart from the indicator area and the reference area 76 on the reference surface 72, consists in particular of polytetrafluorethylene PTFE, which in particular is marketed by DuPont under the brand name Teflon, or of silicon. Both PTFE sand silicon can be filled with white or colored pigments or dyes.

Figure 2:
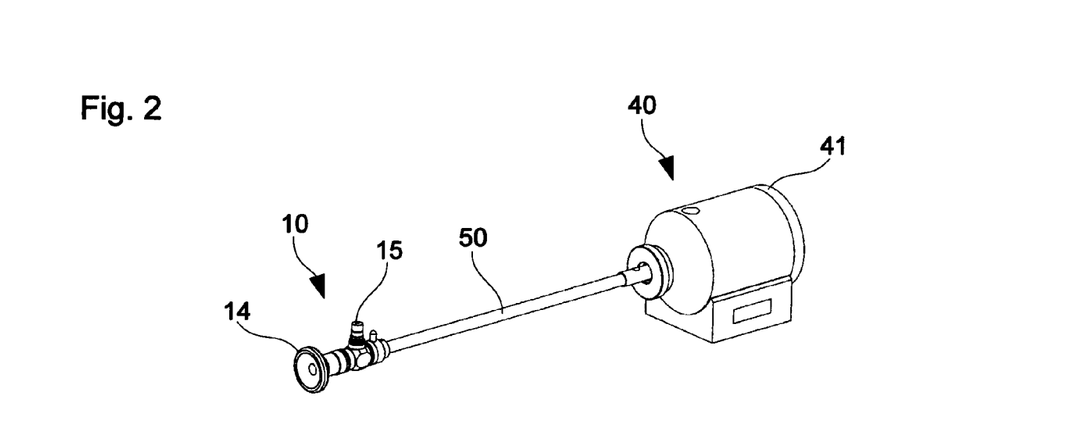
FIG. 2 is a schematic depiction of an endoscope with a test apparatus.

FIG. 2 shows a schematic axonometric depiction of an endoscope 10 and a test apparatus 40 that are similar to the endoscope and test apparatus presented above with reference to FIG. 1. Contrary to FIG. 1, no separate light source, video camera or other apparatuses are shown. The positioning device 50 in the example shown in FIG. 1 extends all the way to the proximal end 11 of the endoscope 10 and occupies the entire shaft of the endoscope 10. The exact positioning of the distal end of the endoscope 10 in the test apparatus 40 in this example is achieved by form-locking between the positioning device 50 and the distal end 11 of the endoscope 10, in particular by means of a mechanical stop and/or a catch-lock connection.

Figure 3:
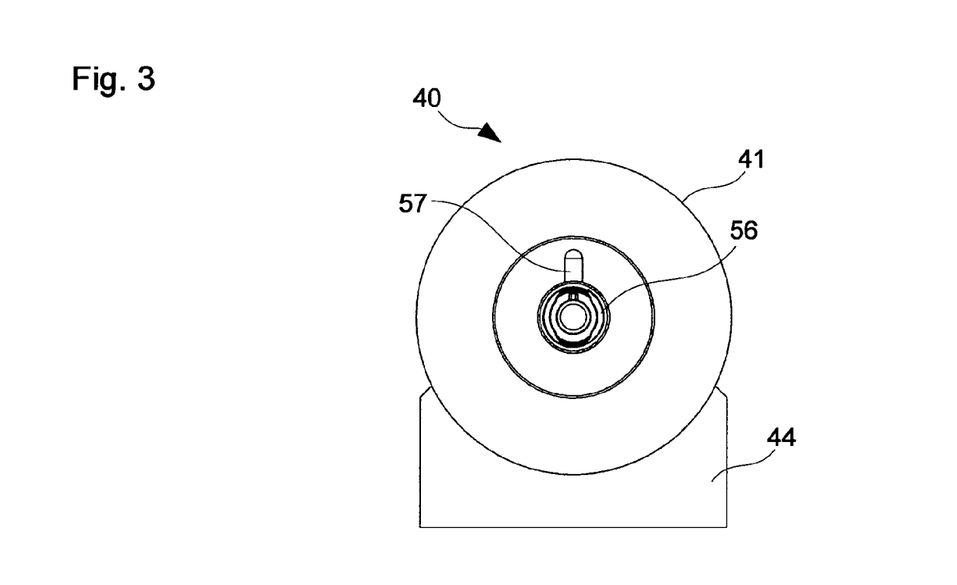
FIG. 3 is a schematic depiction of a test apparatus.

FIG. 3 shows a schematic view of the test apparatus 40 shown in FIG. 2 from the direction from which an endoscope 10 can be inserted into the test apparatus 40. This direction is parallel to the longitudinal axis of the shaft 17 of the endoscope 10. The circular contour or in sections cylindrical external shape of the housing 41 is recognizable. To make possible a secure placement of the test apparatus 40, a foot 44 is integrated into the housing 41 or is durably mechanically connected with it. The arrangement and function of a stop 56 for an endoscope 10 and of a ball catch-lock device 57 can be better recognized in FIG. 4.

Figure 4:
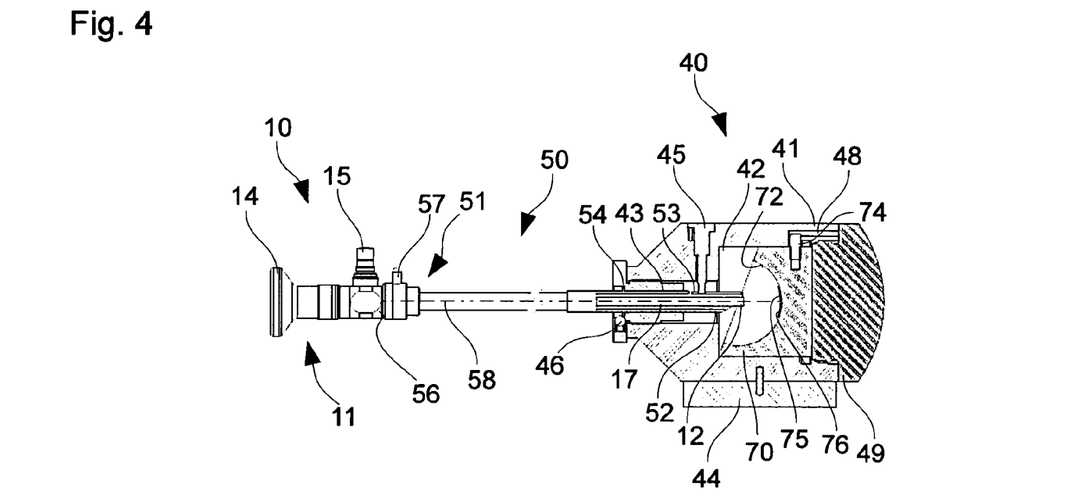
FIG. 4 is a schematic depiction of a test apparatus with an endoscope.

FIG. 4 shows another schematic depiction of the configuration, shown axonometrically in FIG. 2, of the test apparatus 40 and endoscope 10. FIG. 4 shows a view from a direction perpendicular to the longitudinal axis of the shaft of the endoscope 10. The test apparatus 40 is shown in a longitudinal section in such a way that the plane of intersection contains the longitudinal axis of the shaft of the endoscope 10.

Clearly recognizable in FIG. 4 are the housing 41, the hollow space 42 in the housing 41, the aperture 43 to the hollow space 42, the foot 44, a pin 45, a ball catch-lock device 46 on the outer end of the aperture 43, a groove 48 and a screw-in lock 49 on the side of the housing 41 turned away from the aperture 43. Also recognizable is the reference body 70 with the reference surface 72 and a pin 74. The screw-in lock 49 closes off the hollow space 42. The screw-in lock 49 closes off the hollow space 42. When the screw-in lock 49 is opened, the reference body 70 can be removed from the hollow space 42. The hollow space 42 and reference body 70 are then ideally accessible with all their surfaces for cleaning and sterilization. When the reference body 70 is inserted into the hollow space 42, the pin 74 engages in the groove 48 so that the reference body 70 assumes a predetermined position and cannot rotate in the hollow space 42.

It can also be recognized in FIG. 4 that an end 52 of the positioning device 50 extends through the aperture 43 into the hollow space 42 of the test apparatus 40. The positioning device 50 is essentially exactly as long as the shaft 17 of the endoscope 10. The positioning device 50 thus guides and holds the shaft 17 of the endoscope over its entire length. In the foreseen position of the endoscope 10, a portion of the outer surface of the endoscope 10 close to the proximal end 11 is contiguous with a stop 56 on the positioning device 50. Simultaneously, a spring-loaded ball of the ball catch-lock device 57, not shown in FIG. 4, engages in a recess on the endoscope 10 close to its proximal end 11. Thus the position of the endoscope 10 is secured in relation to the positioning device 50. Depending on the shape of the recess in the endoscope 10, in which the ball catch-lock device 57 engages on the end 51 of the positioning device 50 turned away from the hollow space 42 of the test apparatus 40, this catch connection can simultaneously prevent a rotation of the endoscope around the longitudinal axis of the shaft 17.

The end 52 of the positioning device 50 turned toward the hollow space 42 of the test apparatus 40 is essentially cylindrical and, with respect to the correspondingly shaped aperture 43 in the housing 41 of the test apparatus 40, has little play. A longitudinal axis 58 of the positioning device 50, when an endoscope 10 is inserted into the positioning device 50, is parallel to or identical with a longitudinal axis of the endoscope 10. With the positioning device 50 in the foreseen position, a collar 54 on the positioning device 50 is contiguous with a surface foreseen for the purpose on the housing 41 of the test apparatus 40 and is held there by a ball catch-lock device 46. At the same time, the pin 45 inserted into the housing 41 engages in a slit or a groove 53 in the positioning device 50.

Thus the pin 74 on the reference body 70 and the groove 48 in the housing 41, the pin 45 on the housing 41 and the groove 53 in the positioning device 50, the collar 54 on the positioning device 50 and the ball catch-lock device 46 on the housing 41 as well as the stop 56 and ball catch-lock device 57 in connection with a recess in endoscope 10 not shown in FIG. 4 ensure that the distal end 12 of the endoscope 10 is situated at a predetermined position and direction relative to the reference surface 71 in the test apparatus 40.

Figure 5:
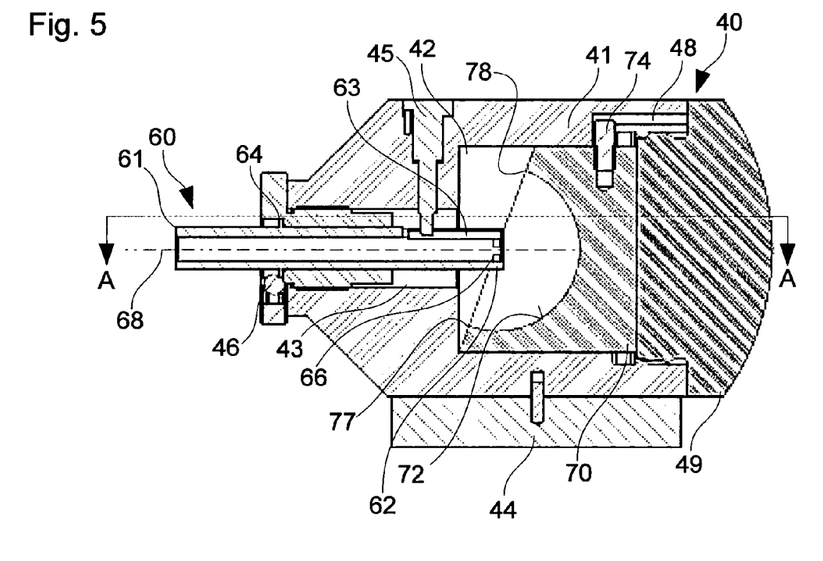
FIG. 5 is a schematic depiction of a test apparatus.
Figure 6:
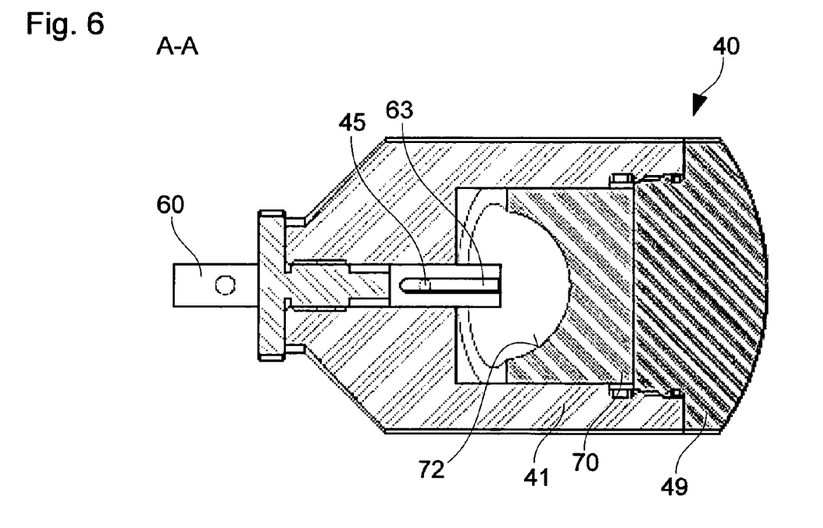
FIG. 6 is another schematic depiction of the test apparatus from FIG. 5.

FIGS. 5 and 6 show schematic depictions of a second test apparatus 40 in two different sections. The plane of intersection shown in FIG. 5 corresponds to the plane of intersection to the right in FIG. 4. The plane of intersection A-A shown in FIG. 6 is indicated in FIG. 5 and stands perpendicular to the plane of intersection of FIG. 5.

The test apparatus 40 shown in FIGS. 5 and 6 is differentiated from the test apparatus shown above in that another positioning device 60 is inserted into the aperture 43 in the housing 41. The housing 41, hollow space 42, aperture 43, foot 44, pin 45, ball catch-lock device 46, groove 48, screw-in lock 49 and reference body 70 correspond to those of the test apparatus described above with reference to FIGS. 2 through 4.

The positioning device 60 shown in FIGS. 5 and 6 is substantially shorter than the positioning device 50 presented above with reference to FIGS. 2 and 4. The end 61 of the positioning device 60 turned away from the hollow space 42 in the housing 41 extends only a little beyond the aperture 43. A mechanical stop 66 in the form of a collar that reduces the lumen of the positioning device 60 is positioned on the end 62 of the essentially tubular positioning device 60 that extends into the hollow space 42. The positioning device 60, similarly as the positioning device 50 presented above, is held on the housing 41 of the test apparatus 40 by reciprocal action of a collar 64 with the ball catch-lock device 46. The pin 45 on the housing 41 engages in a groove 63 in the positioning device 60. When an endoscope 10 is inserted into the positioning device 60, a longitudinal axis 68 of the positioning device 60 is parallel to or identical with a longitudinal axis of the endoscope 10.

The positioning device shown in FIGS. 5 and 6 is configured to position a distal end of a flexible endoscope with respect to the reference surface 72. A comparison of FIGS. 4 through 6 clearly shows that the positioning devices 50, 60 on the test apparatus 50 can be interchanged with one another. This does not require a tool; the positioning devices 50, 60 must only be pushed against the catch force of the ball catch-lock device 46 into the housing 41 of the test apparatus 40 or pulled out of it. Aside from positioning devices for rigid endoscopes with a certain shaft length and a certain shaft diameter, and for flexible endoscopes with a certain shaft diameter, other positioning devices can be inserted into the aperture 43 of the housing 41 for other shaft diameters or other shaft lengths.

Another aspect of the simple removability and insertability of the positioning devices 50, 60 is that the test apparatus 40 can easily be dismantled and all components including the positioning device 50, 60 can easily be cleaned and—for example by autoclaving—sterilized. Also significant for this is the fact that after removing the screw-in lock 49, the reference body 70 can be removed from the hollow space 42. No tool is required in order to disassemble and reassemble the test apparatus 40.

A particular aspect of the test apparatus shown in FIGS. 4 through 6 is that the reference surface 72 constitutes a portion of a spherical surface. The positioning devices 50, 60 are configured in such a way that the distal end 12 of an endoscope 10 inserted into the positioning device 50, 60 is positioned at the center point of the spherical surface and thus is at the same distance from all points of the reference surface 72. A few endoscopes have a curved object field; that is, the quantity of points that can simultaneously be imaged sharply (for example, on an image sensor of a video camera 31) forms a curved surface. The curvature of this surface, in particular, is adapted to the typical curvature of a surface of an object that the endoscope is intended to observe. The curvature of the reference surface 72 and its radius or distance from the distal end 12 of the endoscope 10 can be adapted to the object field curvature of the endoscope 10 for which the test apparatus 40 is intended. This simplifies the focusing of the endoscope inserted into the test apparatus 40.

In addition, because of the spherical shape of the reference surface 72 and the expected position of the distal end 12 of the endoscope at the center point of the spherical surface, the distance of the point on the reference surface 72 that lies in the center of the image generated by the endoscope 10 from the distal end 12 of the endoscope 10 is independent of the line of vision of the endoscope. The test apparatus 40 can thus be used for endoscopes with different lines of vision.

It can also be seen in FIGS. 4 through 6 that the edge (in FIGS. 4 and 5, in particular, the straight line in the projection on the illustrated plane of intersection between points 77, 78) of the reference surface 72 does not lie in a plane perpendicular to the longitudinal axis 58, 68 of the positioning device 50, 60. Instead, the edge of the reference surface 72 lies in a plane whose normal forms an angle of approximately 30 degrees to the longitudinal axis 58, 68 of the positioning device 50, 60. This enlarges the spectrum of possible lines of vision of endoscopes for which the test apparatus 40 can be used. For example, in this angle the test apparatus can also be used for an endoscope whose line of vision forms an angle of 90 degrees to its longitudinal axis and whose visual field is 60 degrees wide. Because of still greater angles between the normal of the plane in which the edge of the reference surface 72 lies and the longitudinal axis 58, 68 of the positioning device 50, 60, the spectrum of possible lines of vision of the endoscopes to be examined can be further enlarged. At the same time the semi-spherical reference surface 72 can be easily produced, for example by casting or by means of machining methods, without any need to produce indentations.

It is especially important for the cited advantages of the tipped arrangement of the reference surface 72 that the straight line is tipped by opposite points or sites 77, 78 on the edge of the reference surface 72 with respect to the longitudinal axis 58, 68 of the positioning device 50, 60. The shape of the edge of the reference surface 72 between these two points 77, 78 can depart from a level circular ring without reducing the aforementioned advantages. In a generalization of this consideration, the reference surface 72, instead of the shape of a portion of a spherical surface, can have the shape of a portion of a cylindrical surface. In this case the cylindrical axis of the cylindrical surface is in particular perpendicular to the plane of projection of FIGS. 4 and 5. The straight line between the points 77, 78 then no longer constitutes the edge of the reference surface 72 but instead a connecting straight line of points 77, 78, which forms an angle of 60 degrees, for example, to the longitudinal axis 58, 68 of the positioning device 50, 60.

Hereafter, on the basis of FIGS. 7 through 10, methods for testing an optical investigation system are described that can be executed by means of the test apparatus 40 described above. First, on the basis of FIGS. 7 and 8 spectra are presented, and on the basis of FIGS. 9 and 10 white balance parameters are presented, on the basis of which a functionality or another property of the optical investigation system can be determined.

Figure 7:
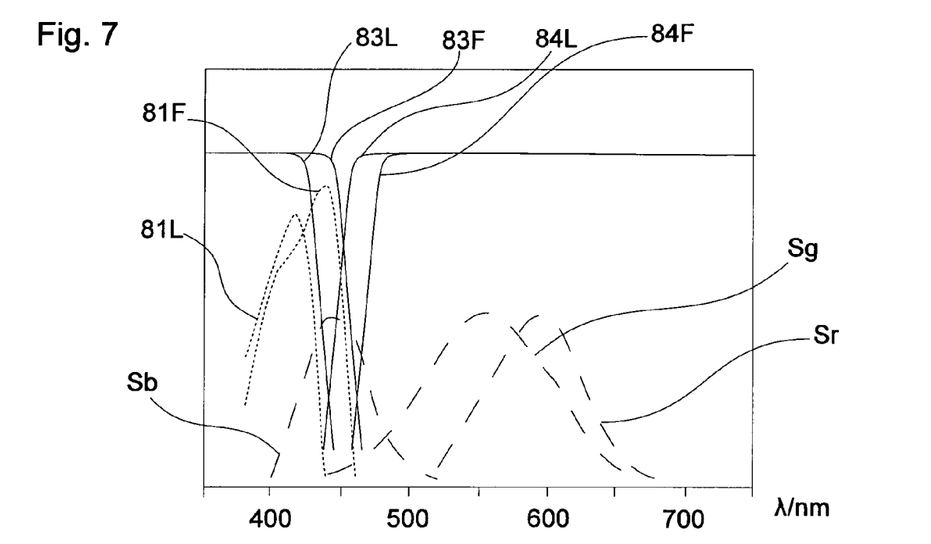
FIG. 7 is a schematic depiction of several spectra.

FIG. 7 shows a schematic depiction of fluorescence-excitation spectra as well as transmission spectra of illumination and observation filters, which are used for different types of fluorescence diagnostics. The wavelength lambda is plotted on the abscissa axis. In addition to the fluorescence-excitation spectrum 81L, the transmission spectrum 83L, the illumination filter and transmission spectrum 84L of the observation filter for PDD, the figure also shows the fluorescence-excitation spectrum 81F, the transmission spectrum 83F of the illumination filter and the transmission spectrum 84F of the observation filter for observing autofluorescence (AF) of tissue.

In addition, FIG. 7 shows spectral sensitivities Sb, Sg, Sr of the blue, green and red color receptors of the human eye. Because cameras as far as possible are adapted to the color reception of the human eye, as a rule they have similar spectral sensitivities. In comparing the transmission spectra 83L, 83F, 84L, 84F of the illumination and observation filters for PDD and AF with the spectral sensitivities of the color receptors of the human eye, it becomes clear that the small differences between the transmission spectra of the illumination and observation filters for PDD and AF are recognizable to the human eye only under good conditions in immediate comparison—which is seldom possible.

Figure 8:
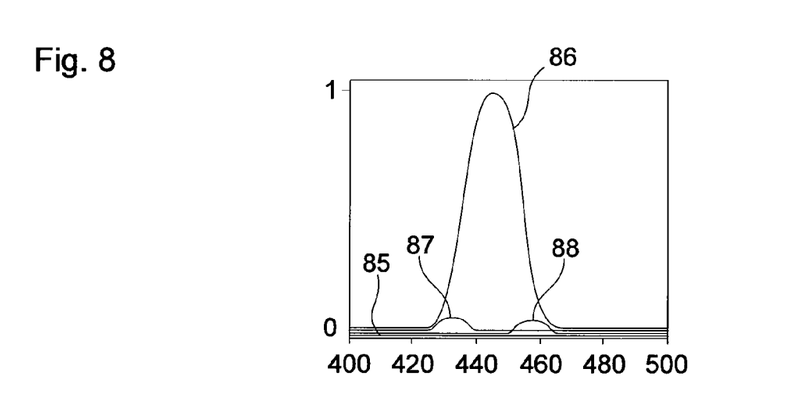
FIG. 8 is a schematic depiction of products of transmission spectra.

FIG. 8 shows a schematic depiction of various products, each of a transmission spectrum of an illumination filter and of a transmission spectrum of an observation filter. The curves are vertically slightly pushed toward one another so that they can be distinguished more easily. In fact, all products at wavelengths around 400 nm and at wavelengths around 500 nm are close to zero.

The product 85 of the transmission spectrum 83L of the PDD illumination filter and the transmission spectrum 84F of the AF observation filter is very small or nearly zero for all wavelengths. Thus the AF observation filter is not transparent for remitted PDD excitation light.

The product 86 of the transmission spectrum 83F of the illumination filter for AF diagnostics and the transmission spectrum 84L of the observation filter for PDD is clearly greater than zero for wavelengths in the range from about 430 nm to about 460 nm. The PDD observation filter is thus transparent for remitted AF excitation light to a clearly visible degree.

The product 87 of the transmission spectrum 83L of the illumination filter for PDD and the transmission spectrum 84L of the observation filter for PDD is not zero in a small wavelength range between about a 430 nm and about 440 nm. The PDD observation filter is slightly transparent for remitted PDD excitation light.

The product 88 of the transmission spectrum 83F of the illumination filter for AF and the transmission spectrum 84F of the observation filter for AF is not zero in a small wavelength range in the area of 460 nm. The AF observation filter is slightly transparent for remitted AF excitation light.

In observing a white, non-fluorescent reference surface with an optic investigation system, it can thus be clearly distinguished under favorable circumstances whether a PDD illumination filter is combined with an AF observation filter or an AF illumination filter is combined with a PDD observation filter. In the first case, an extremely dark image is observed; in the second case, too bright an image is observed in comparison to correct combinations of illumination filter and observation filter. It can scarcely be distinguished, on the other hand, whether an illumination filter for PDD is combined with an observation filter for PDD or an illumination filter for AF with an observation filter for AF. In both cases the image is approximately equally bright; the difference in wavelength in any case can be distinguished by the human eye in very good conditions in an immediate comparison.

Figure 9:
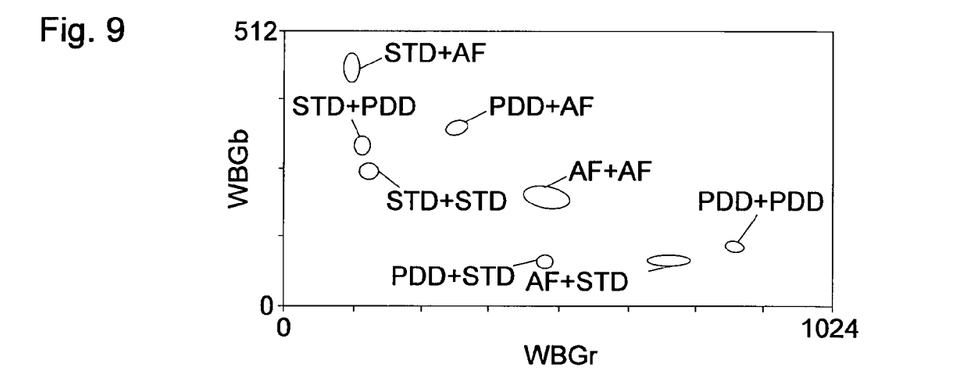
FIG. 9 is a schematic depiction of white balance parameters.

In a schematic diagram, FIG. 9 shows typical white balance parameters after a white balance on a white, non-fluorescent reference surface with various combinations of illumination filters and observation filters. The reference surface in this example is a surface of a reference body of white PTFE. The white balance parameter WBGr is plotted on the abscissa, the white balance parameter WBGb on the ordinate, and the third white balance parameter WBGg according to a convention has the value WBGg=128=0x080. The filter combination in each case is indicated at the measurement points, where the indication before the plus sign refers to the illumination filter and the indication after the plus sign to the observation filter. Thus "STD" means no filter (white light), "PDD" means a filter for PDD and "AF" a filter for AF. Admissible filter combinations are STD+STD, PDD+PDD and AF+AF.

It can be recognized that different filter combinations have different white balance parameters as a consequence, which can be unequivocally assigned and distinguished. After conducting a white balance with an appropriate reference surface, conclusions can thus be drawn from the white balance parameter concerning the present filter combination.

Because the white balance parameters vary from camera type to camera type and in some cases even from camera to camera, the white balance parameters obtained from a white balance can, for example, be corrected by corrective parameters filed in the camera. Corrective parameters filed in the camera are, for example, white balance parameters obtained on a white surface without illumination and observation filter. These corrective parameters can be filed in the camera control device 35 instead of in the camera 31. Additional corrections can ensue for the structural form or the type of endoscope, because rigid and flexible endoscopes, endoscopes with different diameters or for different applications have different transmission spectra in the illumination beam path and in the observation beam path.

In using a non-white reference surface for a white balance, the precision or reliability of the differentiation of various filter combinations can be further improved on the basis of the white balance parameters. This is true in particular when edges or flanks in absorption or fluorescence excitation spectra lie in proximity to filter edges of the illumination and observation filters that are to be differentiated.

Figure 10:
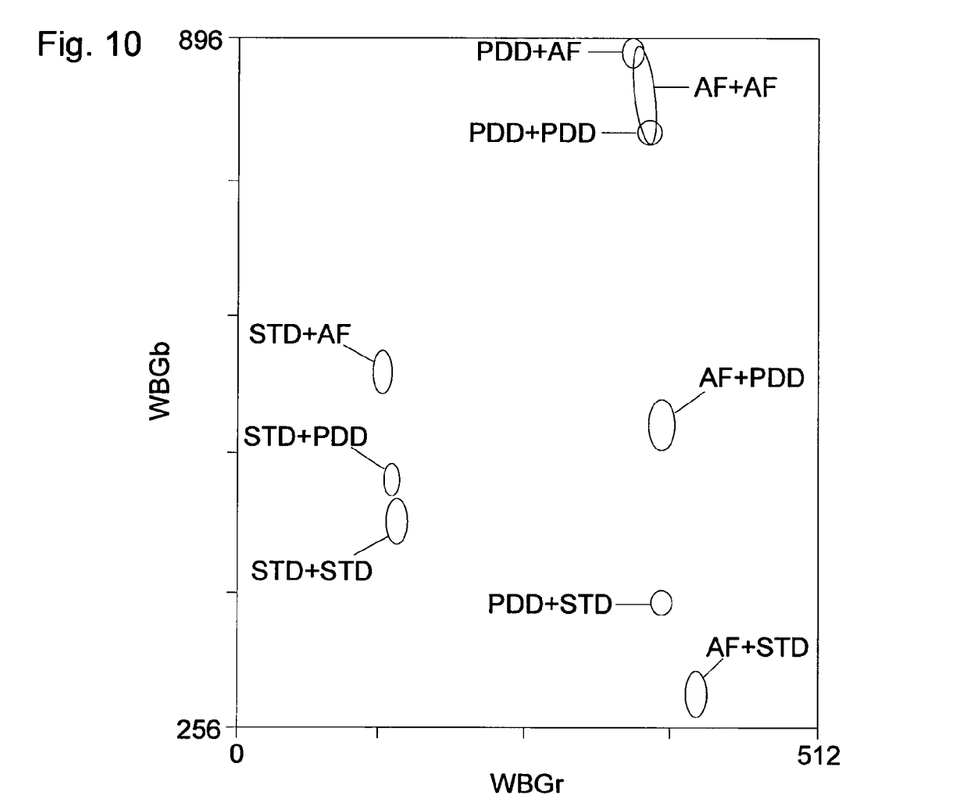
FIG. 10 is a schematic depiction of additional white balance parameters.

In a schematic diagram, FIG. 10 shows white balance parameters for various filter combinations in a white balance on a reference surface made up of a covering layer of Maragloss GO 320 Fluoresco Yellow paint produced by Marabu. Abscissa and ordinate as well as designations of measured values correspond to those of FIG. 9. A comparison of FIGS. 9 and 10 shows that an especially secure identification of the existing filter combination is possible if both the white balance parameters from a white balance on a Teflon surface and the white balance parameters from a white balance on a covering layer of Marabu Maragloss GO Fluoresco 320 yellow are combined. Additional improvements are also possible, for example, by a logical or algebraic linking of the white balance parameters.

Figure 11:
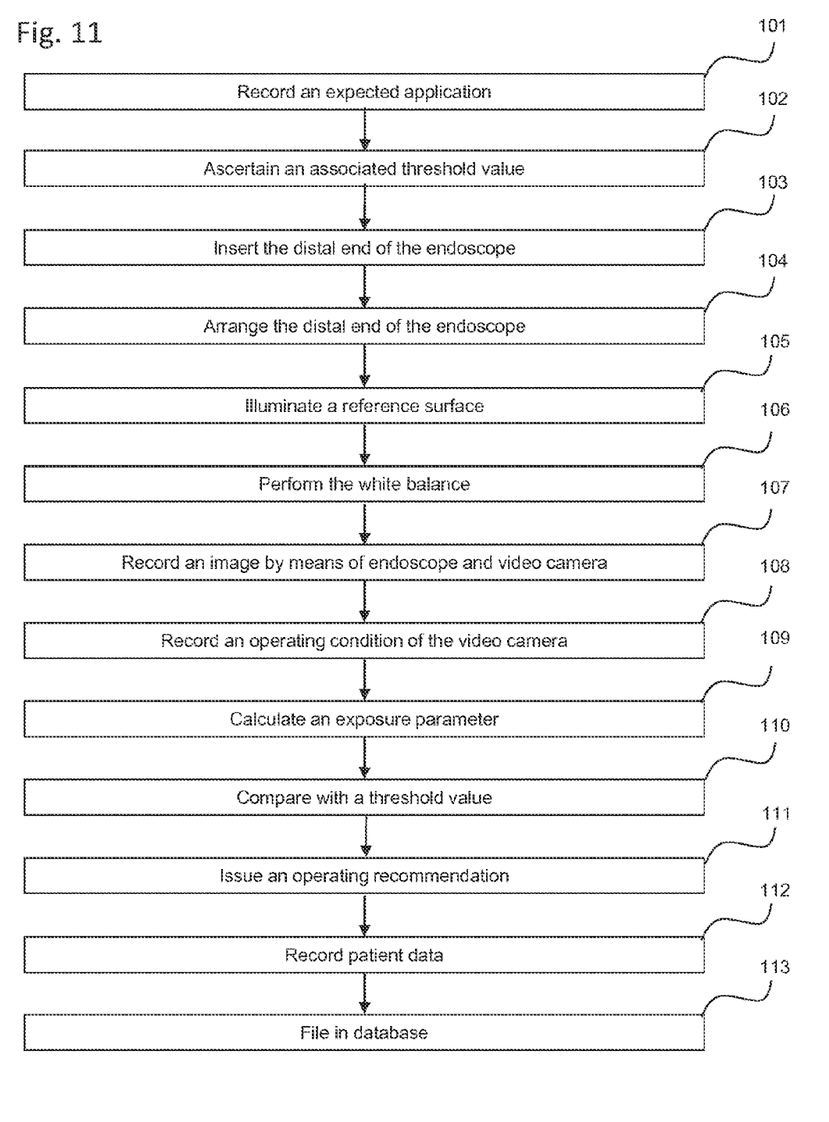
FIG. 11 is a schematic flow diagram.

FIG. 11 shows a schematic flow diagram of a method for testing an optical investigation system, with an imaging device, a video camera and a light source for optical investigation of an object. Although the method can also be applied to optical investigation systems with test apparatuses that differ from those described above, hereinafter reference numbers from FIGS. 1 through 6 are used as examples for greater clarity. In the method, features of spectra are used as illustrated in FIGS. 7 and 8 and of white balance parameters as shown in FIGS. 9 and 10 in order to test the functionality of the optical investigation system or to determine another property of the optical investigation system, for example illumination and observation filters contained therein.

In an optional first step, an expected application of the optical investigation system is recorded, for example on a user interface after a corresponding request. In an optional second step, a requirement associated with the expected application is ascertained on an operating condition of the video camera 31 of the optical investigation system, for example by reading out a look-up table. One or more requirements for the operating condition of the video camera 31 can alternatively be pre-established without modification.

In a third step 103, a distal end of an imaging device, in particular of an endoscope 10, is inserted through an aperture 43 into a hollow space 42 in a light-insulated housing 41. In an optional fourth step 104, which can be executed immediately after the third step 103 or simultaneously with it, the distal end of the imaging device is positioned in a predetermined position and direction in relation to a reference surface 72 positioned in the hollow space 42. This occurs with support from a positioning device, which guides the imaging device 10, in particular its distal end 12, and/or holds it by form-locking or force-locking.

In a fifth step 105, the reference surface 72 is illuminated with illuminating light with an illumination spectrum. If the imaging device is an endoscope 10, the illumination occurs in particular by means of the endoscope or by means of an illumination beam path in the endoscope 10. In an optional sixth step 106, a white balance is conducted, as described above, while the reference surface is illuminated. In the process, white balance parameters, WBGr, WBGb, for example, are selected.

In a seventh step 107, an image is recorded by the imaging device 10 and the video camera 31 during the illumination of the reference surface 72. In an eighth step 108, the operating condition of the video camera 31 that is present during the seventh step 107 is recorded, in particular read out from the video camera 31 or the camera control device 35. Alternatively a noise level or a signal-noise distance in the recorded image, for example, is determined, from which conclusions can be drawn concerning the operating condition of the video camera 31. The operating condition of the video camera includes, for example, white balance parameters WBGr, WBGb, an exposure time valid for all color channels, a gain valid for all color channels, or exposure times and gains valid for individual color channels.

In an optional ninth step 109, an exposure parameter is ascertained, and in particular calculated, from the recorded operating condition of the video camera. For example, an exposure parameter E is calculated from an exposure time T and a gain G according to the formula $E = a \cdot T^b \cdot G^c$. In a likewise optional tenth step 110, the ascertained exposure parameter is compared with one or more threshold values that are associated with an expected application or are generally valid. Alternatively or in addition, the operating condition of the video camera or the parameters that characterize it are compared with other requirements that are associated with the predetermined application of the optical investigation system or generally valid. The result of the comparison indicates the functionality or another property of the optical investigation system.

If white balance parameters are recorded in the eighth step 108, it is possible on the basis of a comparison of the white balance parameters with threshold values to determine which illumination filter or which illumination spectrum and which transmission spectrum was present in the observation beam path in recording the image. For this purpose the threshold values lie, in particular, between the recognizable areas in FIGS. 9 and 10 for example, which are associated with the various filter combinations.

If exposure times, gains or other parameters are recorded in the eighth step 108 that are associated with individual color channels, these parameters of the operating condition, similarly as white balance parameters, are dependent on existing filter combinations. From the parameters of the operating condition associated with individual color channels, therefore, it is likewise possible to draw conclusions concerning the present filter combination. For this purpose the parameters of the operating condition associated with the individual color channels or exposure parameters calculated from them are compared with corresponding threshold values.

In an optional eleventh step 111, a report is issued that can include a statement on the functionality of the optical investigation system, an operating recommendation and/or an operating instruction. In a twelfth step 112, which can also be conducted at any other point in the process, patient data are recorded, for example by means of a user interface. In an optional thirteenth step 113, the patient data, the result of the test method with respect to the functionality or another property of the optical investigation system, and optionally the result of a succeeding or ongoing investigation of a patient are filed in a database by means of the optical investigation system.

In addition, particularly when a video camera 31 is used, model designations, series numbers, software or firmware versions and other data on components of the optical investigation system can be requested over a communication line 39 and filed in the database for documentation or logging. In addition, in the database or separately on another data carrier, the investigation of the patient can be documented or logged. Here images or a video data stream from the camera 31, for example, is filed in the database (for example in MPEG format) or on a videotape.

The invention claimed is:

1. A test apparatus for an optical investigation system, with an imaging device and a light source for optical investigation of an object in remitted light and/or fluorescent light, with:
   a housing with a hollow space and an aperture for inserting a distal end of the imaging device into the hollow space;
   a reference surface with predetermined optical properties in the hollow space, at least either for remission of illuminating light directed onto the reference surface or for emission of fluorescent light;
   a positioning device to hold the imaging device at a predetermined position of the distal end of the imaging device in relation to the reference surface;
   wherein said positioning device comprises a tube having an interior which substantially conforms to the imaging device and an end which is partially closed; and,
   wherein said positioning device has on its end facing the hollow space a mechanical stop that is configured so that the distal end of the imaging device inserted into the test apparatus is at a predetermined position when the imaging device is contiguous with the stop.

2. The test apparatus according to claim 1, wherein the positioning device in addition is configured to prevent rotation of the imaging device inserted into the test apparatus around its longitudinal axis.

3. The test apparatus according to claim 1, wherein the test apparatus is configured in such a way that the positioning device can be separated from the housing and reconnected with it again without use of a tool.

4. The test apparatus according to claim 1, in addition with:
   devices on the housing and on the positioning device for form-locked prevention of rotation by the positioning device around its longitudinal axis.

5. The test apparatus according to claim 3, in addition with:
   a catch-lock device configured to detachably secure the positioning device to the aperture.

6. The test apparatus according to claim 1, wherein the positioning device has on its end turned away from the hollow space a holding device to hold the proximal end of the imaging device inserted into the test apparatus.

7. The test apparatus according to claim 1, wherein the reference surface constitutes a portion of a spherical surface, so that the position foreseen for the distal end of the imaging device is at the center point of the spherical surface; or constitutes a portion of a cylindrical surface, so that the position foreseen for the distal end of the imaging device is on the axis of symmetry of the cylindrical surface.

8. The test apparatus according to claim 1, wherein
the reference surface constitutes a portion of a spherical surface, so that two opposite sites on the edge of the reference surface lie on a straight line that forms an angle in the range of 40 degrees to 80 degrees to the longitudinal axis of the imaging device held by the positioning device; or
the reference surface constitutes a portion of a spherical surface, so that the edge of the reference surface lies in a plane whose normal forms an angle in the range of 10 degrees to 50 degrees to the longitudinal axis of the imaging device held by the positioning device; or
the reference surface constitutes a portion of a cylindrical surface, so that a straight line through two opposite edges of the reference surface forms an angle between 40 degrees and 80 degrees to the longitudinal axis of the imaging device held by the positioning device.

9. The test apparatus according to claim 1, wherein the test apparatus can be dismantled and sterilized.

10. The test apparatus according to claim 1, wherein the reference surface is white or includes a white area.

11. The test apparatus according to claim 1, wherein the reference surface is made of polytetrafluorethylene or silicon.

12. A method for testing an optical investigation system, with an imaging device and a light source for optical investigation of an object in remitted light and fluorescent light, with the following steps:
insert the distal end of the imaging device through an aperture into a hollow space in a housing;
arrange the distal end of the imaging device at a predetermined position in relation to a reference surface with predetermined optical properties in the hollow space using a positioning device which comprises a tube having a stopping surface on at least one end;
illuminate the reference surface with illuminating light with a predetermined spectrum by means of the imaging device;
record light remitted by the reference surface by means of the imaging device;
determine the functionality or another property of the optical investigation system on the basis of the recorded remitted light
wherein said imaging device is held at the predetermined position by a positioning device;
wherein said positioning device comprises a tube having an interior which substantially conforms to the imaging device and an end which is partially closed; and,
wherein said positioning device has on its end facing the hollow space a mechanical stop that is configured so that the distal end of the imaging device inserted into the test apparatus is at a predetermined position when the imaging device is contiguous with the stop.

13. The test apparatus according to claim 1, wherein the end which is partially closed comprises a mechanical stop which prevents insertion of the imaging device beyond a certain point.

14. A test apparatus for an optical investigation system, with an imaging device and a light source for optical investigation of an object in remitted light and/or fluorescent light, with:
a housing with a hollow space and an aperture for inserting a distal end of the imaging device into the hollow space;
a reference surface with predetermined optical properties in the hollow space, at least either for remission of illuminating light directed onto the reference surface or for emission of fluorescent light; and,
a positioning device to hold the imaging device at a predetermined position of the distal end of the imaging device in relation to the reference surface;
wherein said positioning device comprises a tube having an interior which substantially conforms to the imaging device and an end which is partially closed; and,
wherein said positioning device has on its end facing the hollow space a mechanical stop that is configured so that the distal end of the imaging device inserted into the test apparatus is at a predetermined position when the imaging device is contiguous with the stop.

15. The test apparatus according to claim 14, wherein said stopping surface comprises a partial closure of said tube.

16. The test apparatus according to claim 14, wherein said stopping surface comprises a proximal end of said tube.

17. The test apparatus according to claim 14, wherein said stopping surface comprises a flared end of said tube.

18. The test apparatus according to claim 14, wherein said stopping surface comprises a flange.

19. The test apparatus according to claim 14, wherein said stopping surface comprises a shoulder.

* * * * *